(12) United States Patent
Sul

(10) Patent No.: US 7,291,178 B2
(45) Date of Patent: Nov. 6, 2007

(54) MODIFIED OXIDE

(75) Inventor: Young-Taeg Sul, Vastra Frolunda (SE)

(73) Assignee: Mediteam Dental AB, Savedalen (SE)

( * ) Notice: Subject to any disclaimer, the term of this patent is extended or adjusted under 35 U.S.C. 154(b) by 309 days.

(21) Appl. No.: 10/724,096

(22) Filed: Dec. 1, 2003

(65) Prior Publication Data

US 2004/0149586 A1 Aug. 5, 2004

Related U.S. Application Data

(63) Continuation of application No. PCT/SE02/01024, filed on May 29, 2002.

(60) Provisional application No. 60/339,310, filed on Dec. 12, 2001.

(30) Foreign Application Priority Data

May 29, 2001 (SE) .................................... 0101910
Dec. 12, 2001 (SE) .................................... 0104213

(51) Int. Cl.
*A61F 2/28* (2006.01)
(52) U.S. Cl. .................................................. 623/23.55
(58) Field of Classification Search ... 623/23.53–23.55
See application file for complete search history.

(56) References Cited

U.S. PATENT DOCUMENTS 5,478,237 A * 12/1995 Ishizawa .................. 433/201.1
5,609,633 A * 3/1997 Kokubo ....................... 424/423
5,837,121 A * 11/1998 Kinard et al. ................ 205/322
6,136,369 A * 10/2000 Leitao et al. ............... 427/2.27
6,207,218 B1 * 3/2001 Layrolle et al. ............ 427/2.27
6,221,111 B1 * 4/2001 Piveteau et al. .......... 623/23.57

FOREIGN PATENT DOCUMENTS

WO   WO 0072777 A1   12/2000

OTHER PUBLICATIONS

Young-Taeg Sul et al., "Qualitative and quantitative observations of bone tissue reactions to anodised implants", Biomaterials, vol. 23, 2002, pp. 1809-1817.
Young-Taeg Sul et al., "Characteristics of the surface oxides on turned and electrochemically oxidized pure titanium implants up to dielectric breakdown: the oxide thickness, micropore configurations, surface roughness, crystal structure and chemical composition", Biomaterials, vol. 23, 2002, pp. 491-501.
Young-Taeg Sul et al., "The electrochemical oxide growth behavior on titanium in acid and alkaline electrolytes", Medical Engineering & Physics, vol. 23, 2001, pp. 329-346.
Y T Sul et al., "Oxidized implants and their influences on the bone response", Journal of Materials Science: Materials in Medicine, vol. 12, 2001, pp. 1025-1031.
Kato, Makoto et al., "On the dental application of titanium-base alloy. 6. Effect of the composition of electrolytic solutions in andoizing the material", STN International, File CAPLUS, CAPLUS accession No. 1992:455890, Document No. 117: 55890, 1992, 40(8/9), pp. 282-290.
Milena Fini et al., "In vitro and in vivo behaviour of Ca- and P-enriched anodized titanium", Biomaterials, vol. 20, 1999, pp. 1587-1594.

* cited by examiner

*Primary Examiner*—Alvin J. Stewart
(74) *Attorney, Agent, or Firm*—Young & Thompson

(57) ABSTRACT

Osteoconductive/osteoinductive titanium/titanium alloy implant comprising an additional element in the titanium oxide, obtained by anodic oxidation. The implant comprises an additional element in the titanium oxide such as calcium, phosphor or sulphur. The invention also relates to a process of producing the implants.

14 Claims, 14 Drawing Sheets

Ca implant

P implant

S implant

MODIFIED OXIDE

FIELD OF THE INVENTION

The present invention relates to calcium-containing, phosphor-containing and/or sulphur-containing osteoconductive/osteoinductive titanium/titanium alloy implants based on surface oxide chemistry modifications of bone-anchored titanium/titanium alloy implants. The invention also relates to a process of producing said implants.

BACKGROUND OF THE INVENTION

Titanium metal is so far the most successfully osseointegrated implant material in long-term clinical performance [Adell R. et al., 1990]. Despite excellent biocompatibility of thin native oxide films on titanium implants [Kasemo B. et al., 1986 and Johansson C. B. 1991], however, it is generally known that native titanium oxide seldom forms a direct chemical bond to bone tissue (often defined as inert ceramic biomaterial) [Li J. et al., 1998]. Various surface processing technologies such as plasma spraying, simple immersion/soaking method, ion implantation beam associated deposition have been applied to improve biocompatibility of titanium implants. Developments of clinical implants based on alterations of the surface chemical properties have been associated with so called 'bioactive implant' coated with bioactive materials such as various species of hydroxyapatite, calcium phosphate compound, bioglass and bioceramic on metal implants [Hench et al., 1990]. However, a number of studies have reported poor long-term biological stability, for instance, a delamination (intra- and interfacial fracture) of such coating materials as well as biodegradation [Albrektsson T., 1998 and Gottlander M., 1994]. Among many surface modification methods, anodic oxidation is a valuable process to enforce the multifactorial biocompatibility such as the oxide thickness, chemical composition, surface morphology, crystallinity, surface roughness change and dielectric constant of the surface oxide in titanium implants [Sul et al. 2000a and 2001b]. The average maximum stress recorded 33 MPA in the mechanical properties of a thick oxide layer [Hala J et al 2000]. Michiaki et al. (1989) and Seishiro (1989) reported the thicker oxide layer in few micrometer to few tens of micrometer with few µm of pore size fabricated in the $H_2SO_4+H_3PO_4$ mixed electrolyte system. The cross-cut structures of the thicker oxide layer measured with Scanning Electron Microscopy (SEM) was characterized to have the network structure of pore channels and connected channel branches.

U.S. Pat. No. 5,478,237 discloses an anodic oxide film containing both calcium and phosphor, which by a further hydrothermal treatment provides a film comprising a calcium phosphate compound such as hydroxyapatite.

WO 98/51231 discloses modified titanium oxide layers of about 10-200 µm and an increased surface oxide crystallinity and roughness.

U.S. Pat. No. 5,354,390 discloses a process of forming an oxide layer using anodic oxidation followed by a heat treatment.

WO 00/72775 discloses coatings including calcium phosphate compounds. According to WO 00/72777 and WO 00/72776, the surface of oxide layer on the titanium includes about 20% titanium, about 55% oxygen and 20% carbon, the rest of the layer is composed of titanium oxide. The used electrolytes are inorganic and organic acid, for instance the $H_2SO_4+H_3PO_4$ mixed electrolyte system. Cross-sections of the titanium oxide layer disclosed in these documents show a very thick layer exhibiting a network of channels, extension of the channels and connected channel branches; However, the purpose of the channels is mainly to allow the administration of a bone-stimulating agent.

There exists a need for a titanium/titanium alloy implant having an oxide layer exhibiting improved surface properties for a faster and stronger osseointegration.

SUMMARY OF THE INVENTION

The object of the present invention is to produce osteoconductive/osteoinductive oxide properties of titanium/titanium alloy implants, leading to faster and stronger osseointegration in clinical performance of bone-anchored titanium/titanium alloy implants and improved clinical success for long-term functional loading in the human body.

This object has been solved by providing a osteoconductive/osteoinductive titanium/titanium alloy implant, obtained by anodic oxidation, said implant comprises an additional element in the titanium oxide, wherein the additional element is chosen from the group consisting of calcium, phosphor or sulphur, said implant exhibits a cross-section of the calcium-incorporated osteoconductive/osteoinductive oxide layer which consists of a double layer structure of an upper porous layer and a lower compact barrier. The porous upper layer exhibits an open structure comprising a plurality of shallow craters.

One aspect of the invention provides a process of producing a osteoconductive/osteoinductive titanium/titanium alloy implant comprising an additional compound as a titanium oxide component, wherein the additional compound is chosen from the group consisting of calcium, phosphor or sulphur, using a electrochemical oxidation method, comprising the steps of:
 a) providing anodic electrochemical oxidation of the titanium/titanium alloy implant in an electrolyte containing at least one of said additional components,
 b) controlling the anodic forming voltage transient with slope (dV/dt), as to produce an oxide layer on said titanium/titanium alloy implant exhibiting a double layer structure of an upper porous layer and a lower compact barrier layer.

Another aspect of the invention provides a method of producing the implants according to the invention, wherein the additional element is chosen from the group consisting of calcium, phosphor or sulphur, comprising the steps of:
 a) controlling the anodic forming voltage transient with slope (dV/dt) of 2 to 0.3 dV/dt, oxide growth constant ($\alpha$, nm/V), the current efficiency ($nm.cm^2/C$), the anodic oxide forming rate (nm/sec);
 b) controlling the intensity and extent of breakdown phenomenon and breakdown voltage,
 c) controlling the incorporation of either calcium, phosphorous or sulphur into the double layer structure of a upper porous and a lower barrier oxide layer by colloidal deposition mechanism,
 d) controlling reinforcement of the mechanical properties of said oxide containing an additional element for long term functional loading in the human body—to strictly confine the anodising time from the first onset of micro arcing phenomenon on the titanium/titanium alloy anode to near anodic forming voltage transient with slope $dV/dt \approx 0.3$, during the different phases of the anodic process;
 e) detecting the first onset of said micro arcing phenomenon of said process during the oxidation;

f) maintain said process by near anodic forming voltage transient with the slope, dV/dt being about 0.3.

Another aspect of the present invention provides a process of producing a osteoconductive/osteoinductive titanium/titanium alloy implant comprising calcium as a titanium oxide component, wherein said titanium/titanium alloy implant is electrochemically anodically oxidised in (a) at least one calcium-containing electrolyte and (b) EDTA (ethylene diamine tetra acetic acid) to yield a calcium-containing implant.

Yet another aspect of the present invention provides a process of producing osteoconductive/osteoinductive titanium/titanium alloy implants comprising phosphor as a titanium oxide component, wherein said titanium/titanium alloy implant is electrochemically anodically oxidised in at least one phosphor-containing electrolyte to yield a phosphor-containing implant.

A further aspect of the present invention provides a process of producing osteoconductive/osteoinductive titanium/titanium alloy implants comprising sulphur as a titanium oxide component, wherein said titanium/titanium alloy implant is electrochemically anodically oxidised in at least one sulphur-containing electrolyte to yield a sulphur-containing implant.

The oxides produced by the process according to the invention demonstrate excellent mechanical strength and do not show a delamination of the oxide film and oxide particles internalised by the inflammatory cells such as microphage and multinuclear giant cell.

The implants in the present invention takes advantage of the stronger and faster osseointegration as proved in animal studies by strong bonding reactions between bone and the modified surface chemistry of titanium oxide by using process according to the invention, and consequently promote highly successful modality in clinical performance of osseointergrated titanium implants. In addition, the implant surfaces in the present invention have the reinforced mechanical strength and overcome a drawback such as the biological delamination/resorption of the coated calcium phosphate and hydroxyapatite on implants, resulting in clinical loosening of implants in bone.

BRIEF DESCRIPTION OF FIGURES

The present invention will now be further illustrated by means of drawings enclosed herewith, wherein.

DETAILED DESCRIPTION OF THE INVENTION

The Micro Arc Anodic Oxidation (MAO) Process

The present invention produces osteoinductive/osteoconductive titanium/titanium alloy implants with additional components (additives: simple calcium, phosphorus, or sulphur compounds) electrochemically incorporated into the titanium oxide surface layer.

Figure 1:
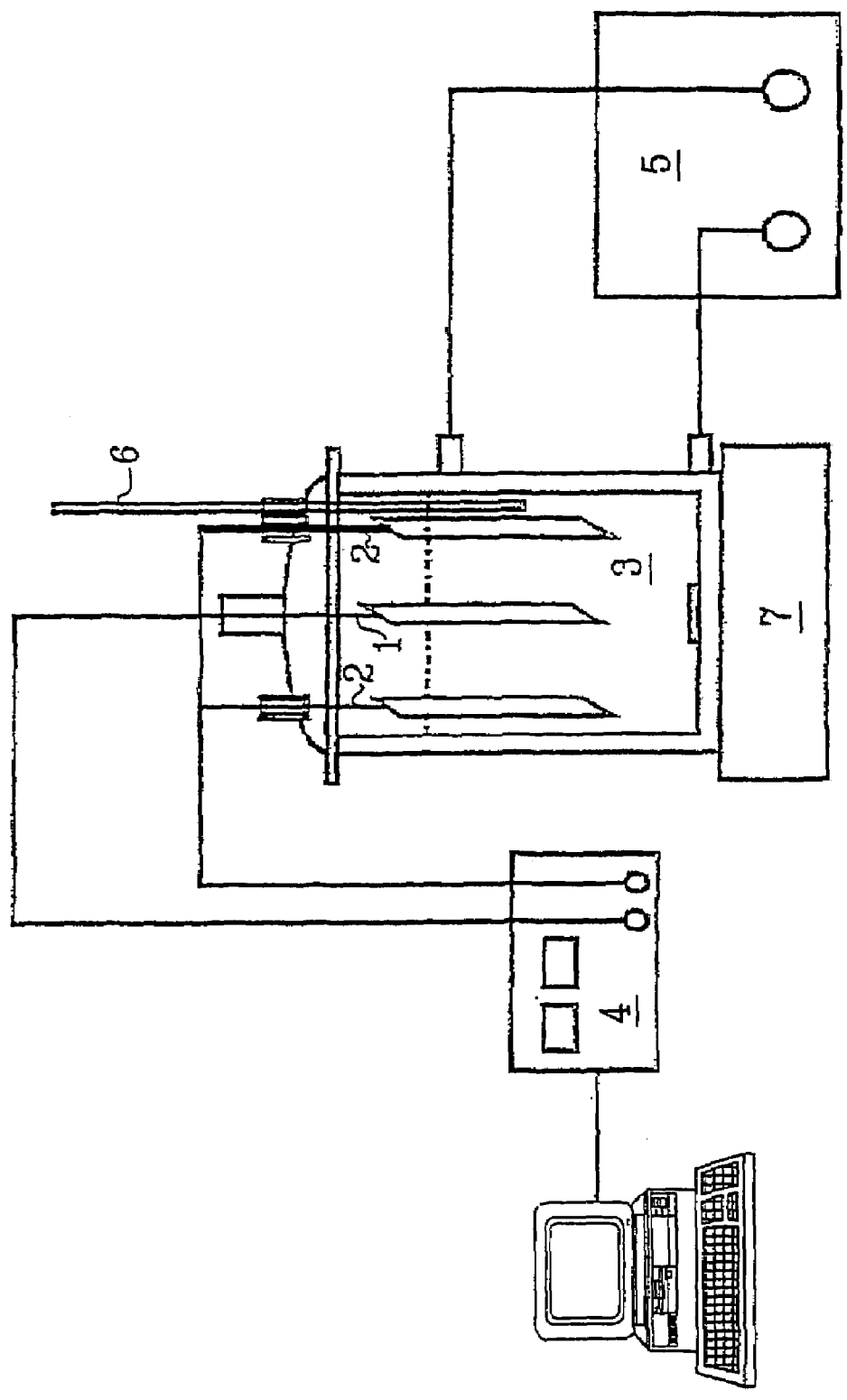
FIG. 1. shows a schematic drawing of the equipment setup.
Figure 2:
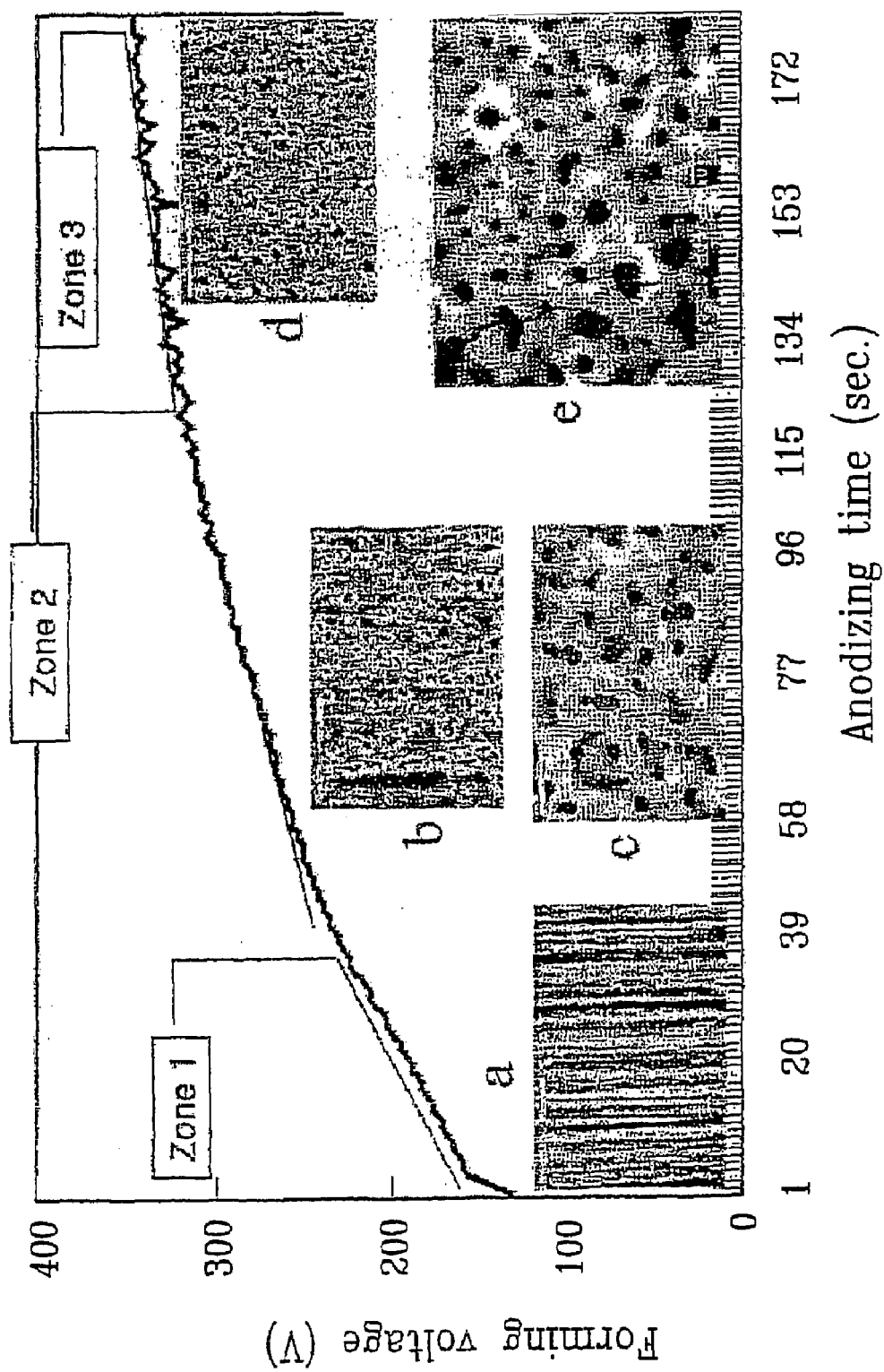
FIG. 2. shows the anode voltage increase in time. The line shows three distinct zones with different slope: Zone 1 is linear with the highest slope; zone 2 is non-linear with slope $dV/dt \geq 0.3$; and zone 3 is non-linear with $dV/dt < 0.3$. Oxide growth characteristics in the three electrochemical zones are exemplified by Scanning Electron Micrographs (SEM) of calcium-incorporated layers. a=barrier oxide film produced in zone 1; b and c=the optimal surface prepared at $dV/dt \geq 0.3$ of zone 2; e=crack-propagated surface obtained in zone 3.

As shown in FIG. 1, the MAO process according to the present invention was performed using an equipment provided with a titanium anode 1 and a platine cathode 2 in an electrolyte 3. A DC power supply 4 was connected to a computer in which electrical current and voltage was recorded every 0.5 second. The temperature was measured using a thermometer 6 and the desired temperature was maintained using a cooling system 5. The electrolyte was stirred using a magnetic stirrer bar 7 on a magnetic stirrer plate 8. During the process the anodic oxide-forming voltage increases with time during three distinguishable phases ("zones") with different slopes dV/dt (FIG. 2): In zone 1 the voltage increases linearly; zones 2 and 3 display transient slopes of $dV/dt \geq 0.3$ and $dV/dt \leq 0.3$, respectively. It was found (see below) that the best results were obtained by strictly confining the anodising time from the first onset of the MAO phenomenon to near the boundary between zones 2 and 3 in FIG. 2, where the slope of the anodic voltage transient is approximately 0.3. This was orchestrated by controlling the following parameters (FIG. 3), given in order of impact on the process: electrical current density>electrolyte concentration>surface area ratio of anode to cathode>electrolyte temperature≧agitation speed>chemical composition of the titanium/titanium alloy electrode (ASTM grade 1-4).

Figure 4:
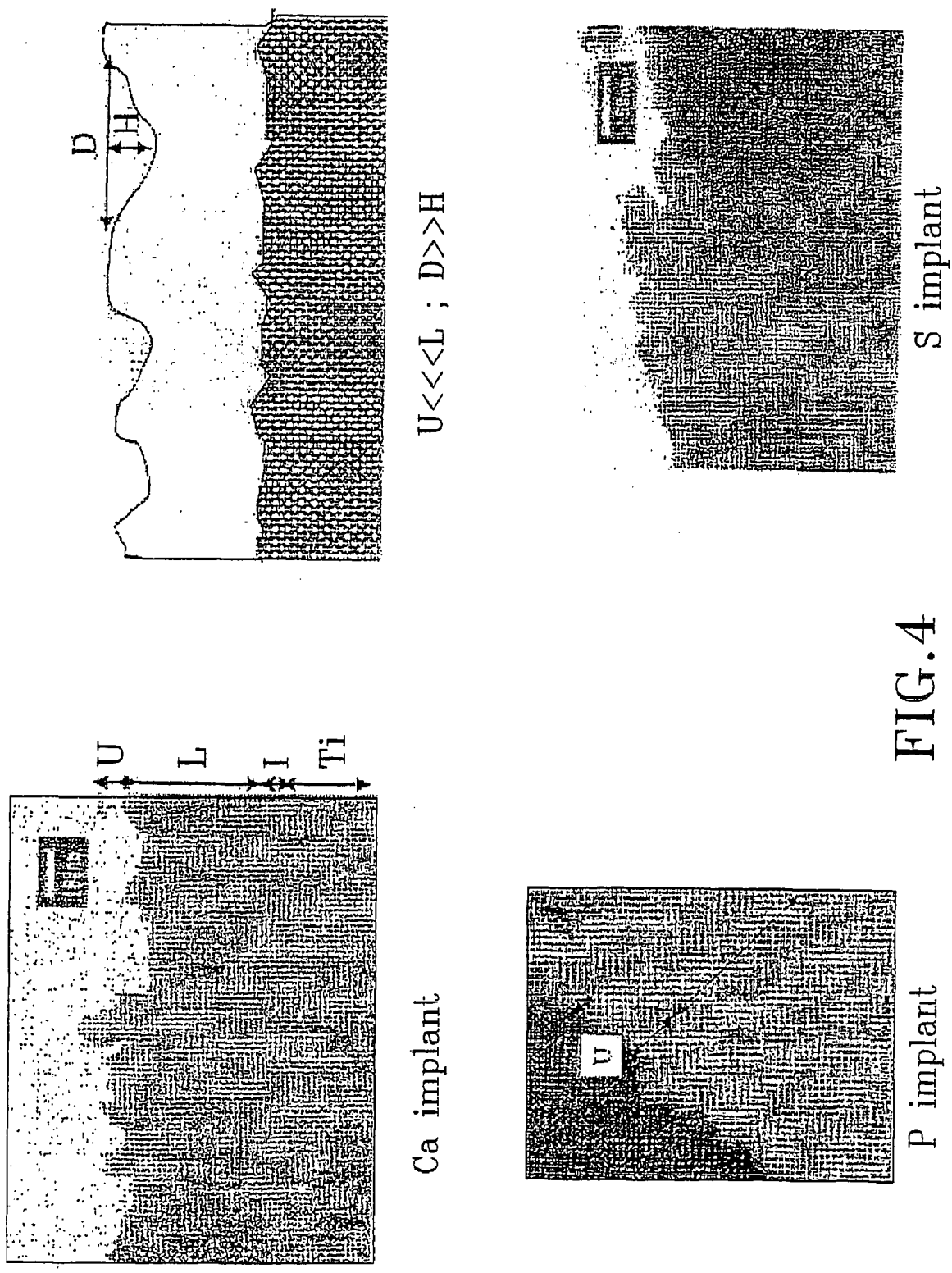
FIG. 4. shows Transmission Electron Micrographs (TEM) of ultramicrotomed cross-sections of the three oxide layer types, in order to demonstrate the double layer structure of each consisting of the upper porous and lower barrier layer, respectively. U=upper porous layer with pores/craters, L=lower barrier layer with no pores/craters, I=titanium/oxide interface, Ti=titanium bulk of the implant, D=width of the pore and H=height of the pore. Thickness of L>>U and size D>>H.
Figure 8:
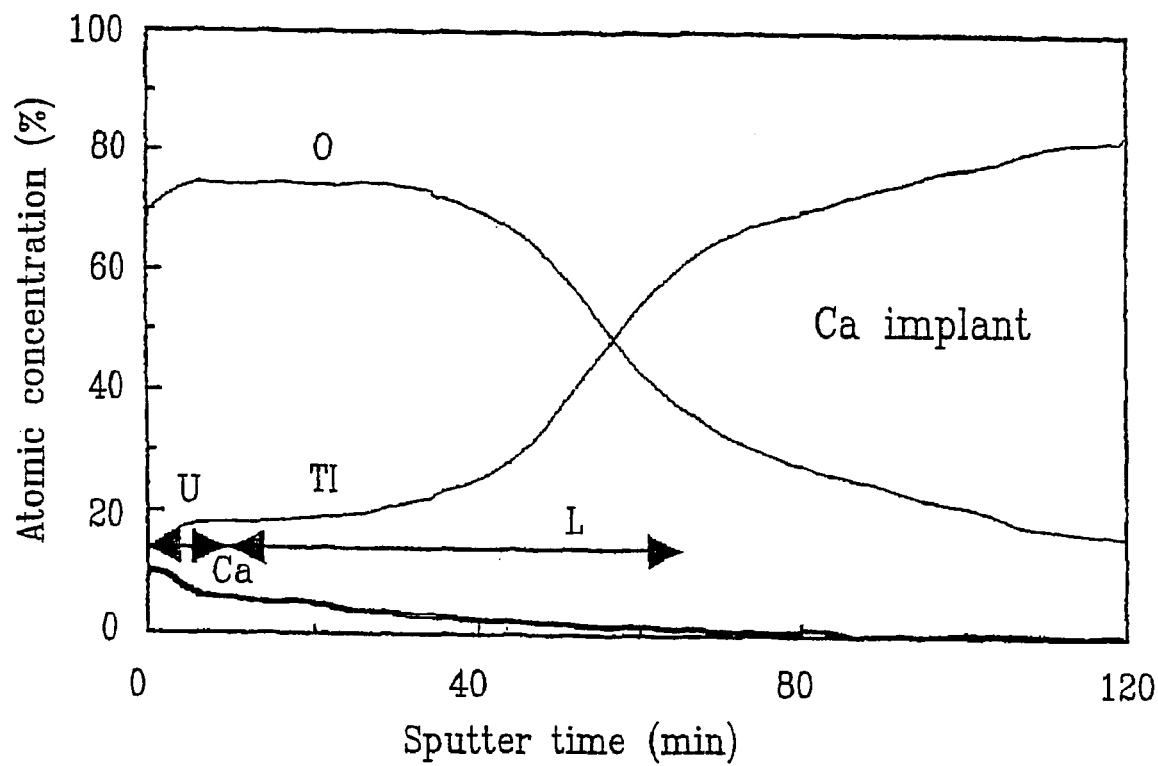
FIG. 8. shows Auger Electron Spectroscopic (AES) measurements of Ca, P, and S concentration depth profiles of the Ca, P and S implants, respectively. U=upper porous layer with pores/craters, L=lower barrier layer with no pores/craters.
Figure 8:
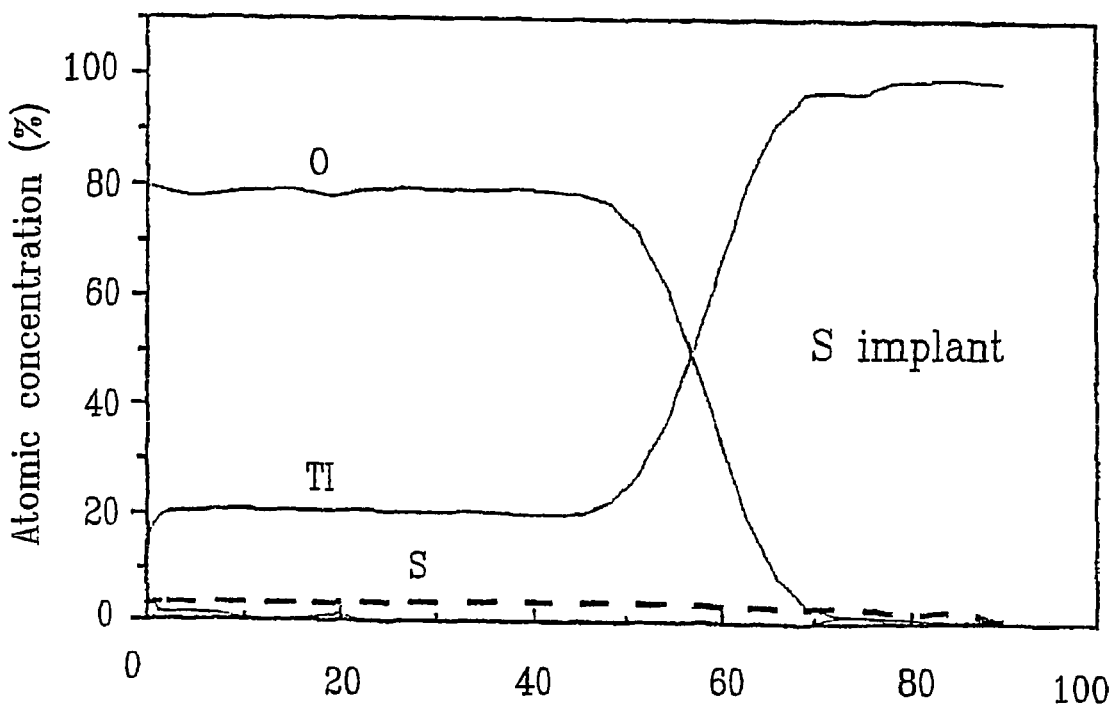
Figure 8:
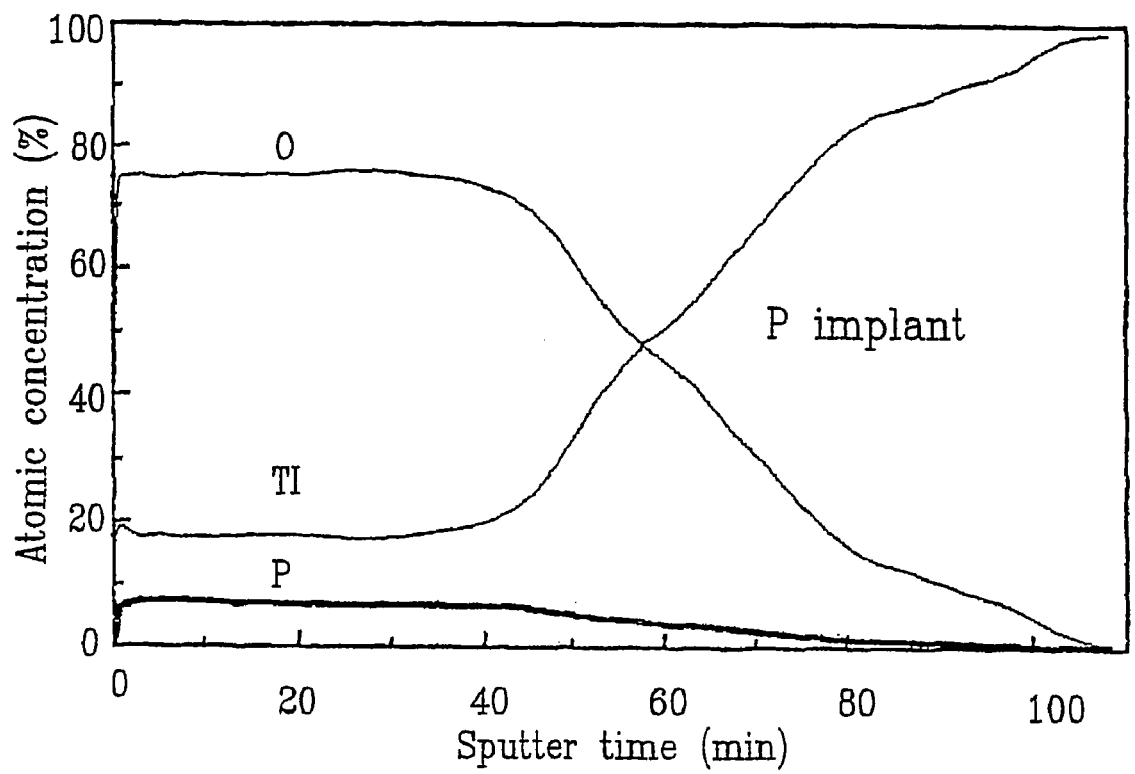
Figure 8:
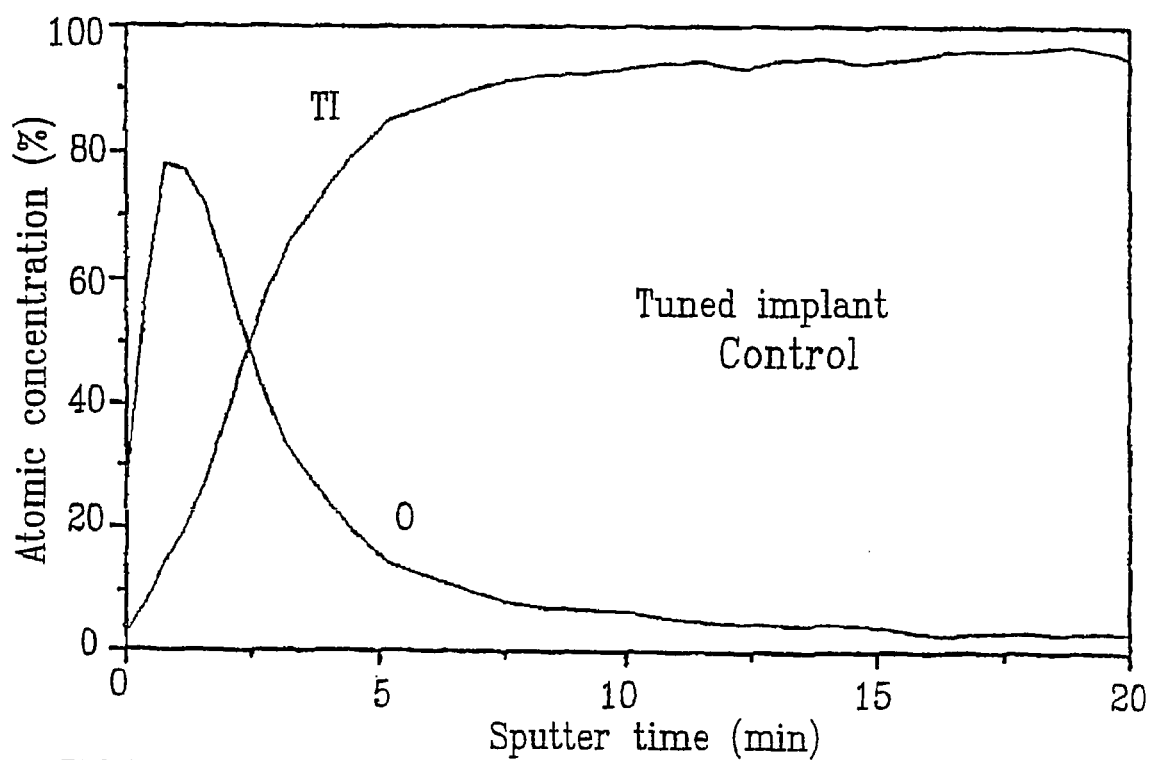

In zone 1 (FIG. 2), the oxide layer grows linearly with the anodic voltage according to the simple relationship $D=\alpha V$, where D is the thickness, $\alpha$ is a growth constant, and V is the voltage. The oxide layer obtained contains lower concentrations of additives (L in the AES depth profiles of FIG. 8) than the layers obtained in zones 2 and 3, and the morphological structure is that of a dense nonporous barrier devoid of pores, craters, and channel networks. This is clearly seen in SEM and TEM micrographs (a in FIG. 2 and L in FIG. 4, respectively). The thickness of this layer is usually between 200-1000 nm (FIGS. 4 and 8).

Figure 5:
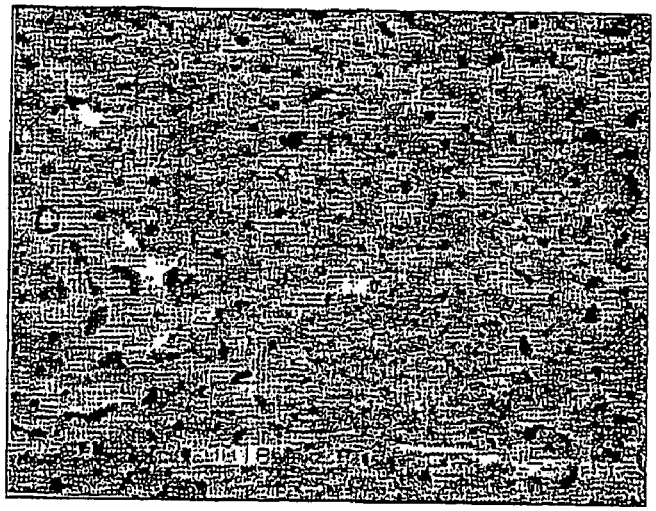
FIG. 5. shows SEM pictures of the surface of Ca, P, and S implants, respectively.
Figure 5:
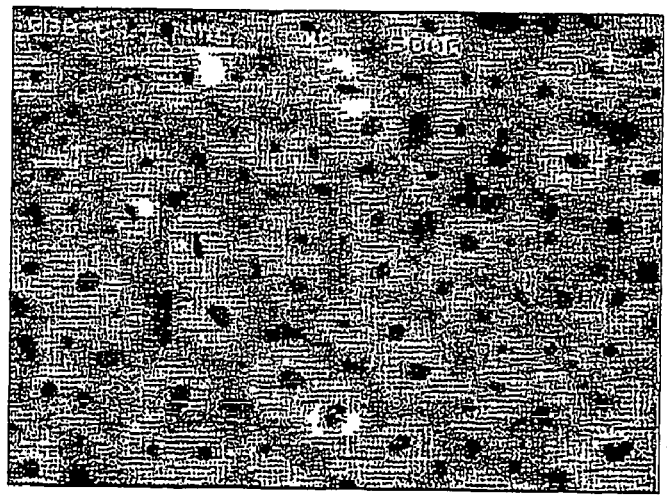
Figure 5:
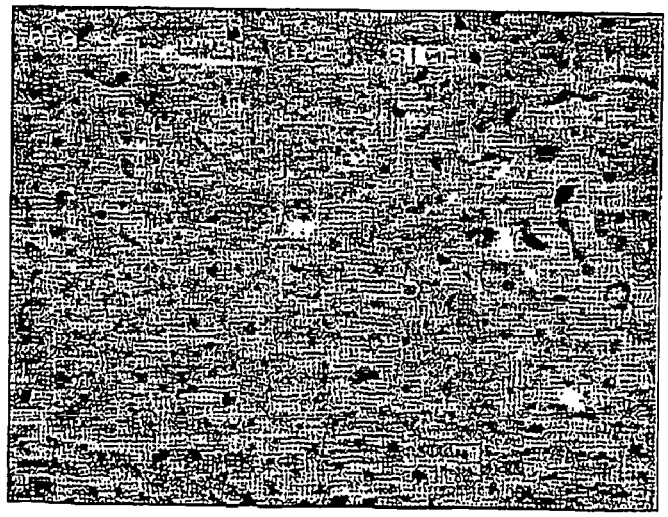

Continuing the anodic oxidation into zone 2 produces an additional oxide layer with different properties on top of the innermost barrier layer. This outer layer has a multitude of pores and craters (b and c in FIG. 2, FIG. 5, and U in FIG. 4) and a higher concentration of additives (U in FIG. 8). Furthermore, it is thinner in than the innermost layer with a thickness lower than 100 nm (FIGS. 4 and 8), and on all MAO-treated surfaces studied the outer layer constituted less than 40% of the two layers taken together.

Stopping the electrochemical oxidation process at dV/dt≈0.3, encompassing zones 1 and 2, thus yields a double-layered oxide surface with optimal morphological and mechanical properties, and this is the case for all three types of additives. If, however, the anodic oxidation is allowed proceed into zone 3 (dV/dt<0.3) the morphology of the oxide layer obtained is somewhat similar to that of zone 2 but it is thicker, and has larger and more numerous pores, craters, and channels (d in FIG. 2). This is the result of the extended breakdown of the zone 3 anodic oxide layer. Such a structure clearly has inferior mechanical properties than those of zones 1 and 2 as is demonstrated by the microcracks in FIG. 2. In addition, it was detected in animal experiments that such a thick oxide film easily delaminates, and the oxide particles released may be internalised into inflammatory cells such as macrophages and multinuclear giant cells (FIG. 6a). On the other hand, the oxide layers with Ca, P, and S additives produced by the MAO process in the present patent claims do not leave unwanted oxide particles in the tissue (FIG. 6b) and they demonstrate excellent mechanical strength, as presented in the experimental section (Table 2).

Electrolytes

The chemical nature of the electrolyte in the electrochemical cell is of less importance, meaning that a large number of Ca, P, and S-containing salts can be used to equally good results as exemplified for calcium in the Experimental section (Table 1). Single electrolytes are used in the solution but any mixture of two or more relevant compounds may also be used.

Figure 7:
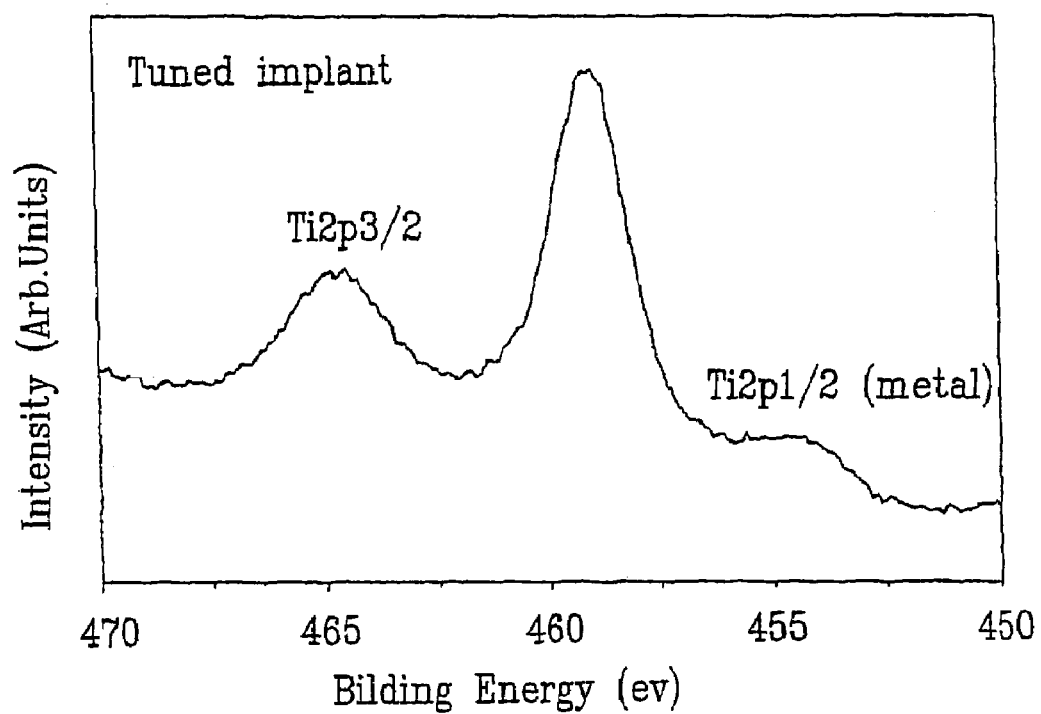
Figure 7:
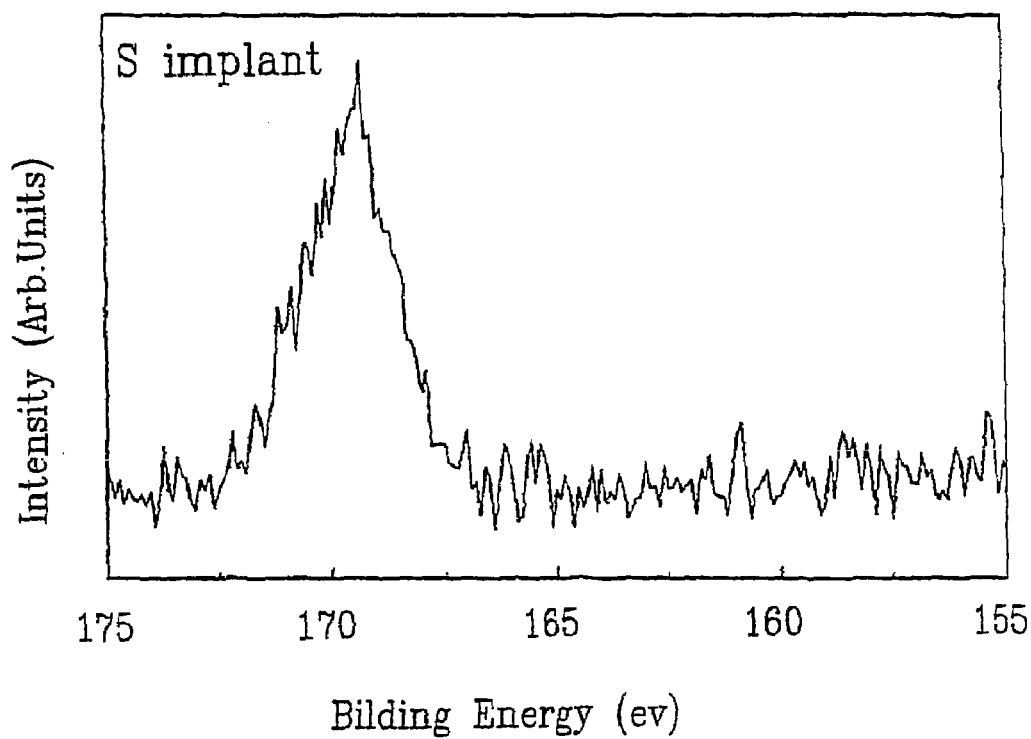
Figure 7:
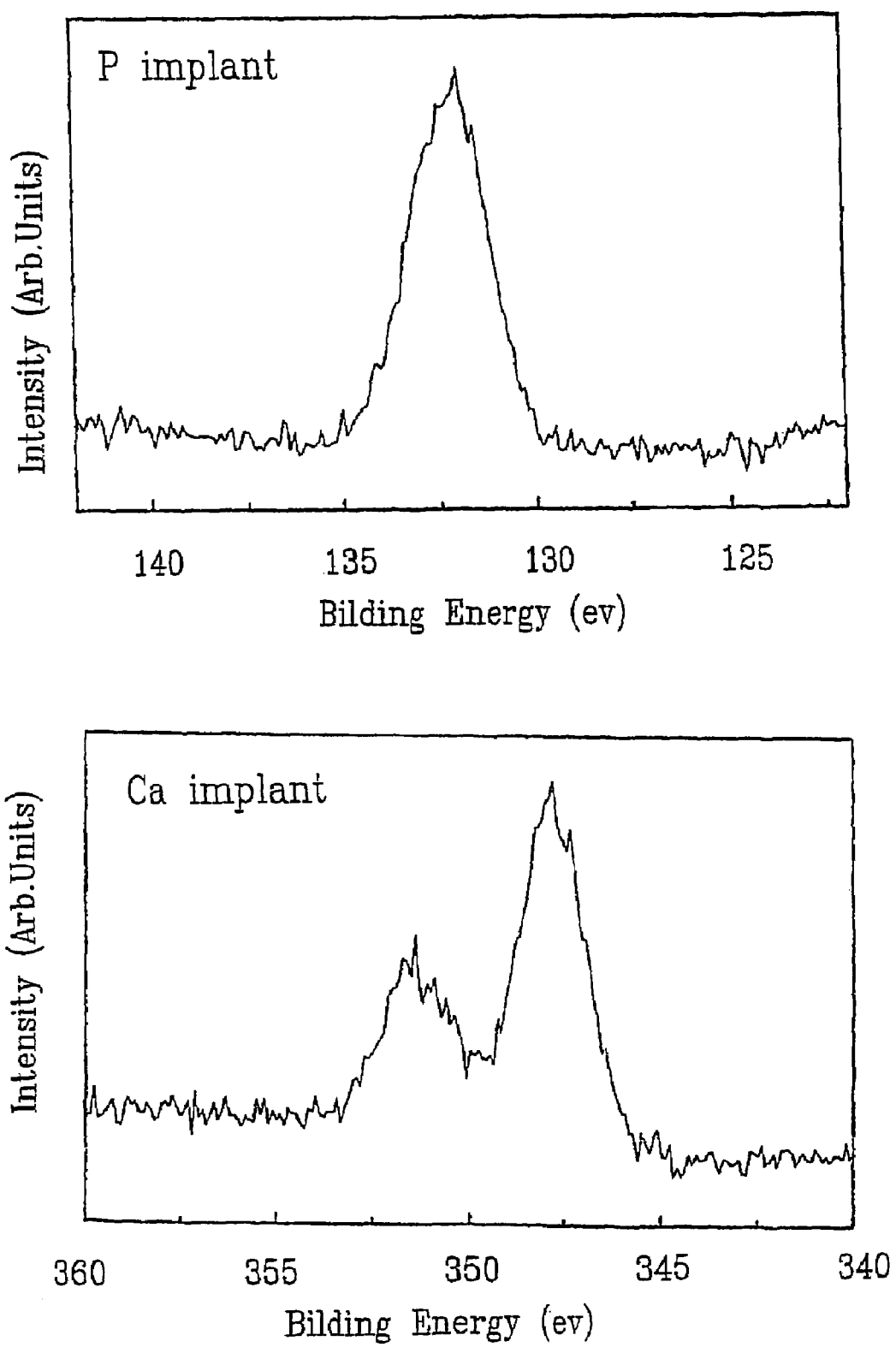

Specifically for calcium, which, as opposed to the phosphorus and sulphur compounds, incorporates into the oxide layer as a one-atomic positively charged ion ($Ca^{2+}$), simple electrolytes (examples 1-5 in Table 1) gave a relative amount of calcium incorporation of less than 10%, as detected by XPS and AES (FIGS. 7 and 8, respectively). For the purpose of increasing the calcium concentration in the oxide layer, the chelating agent EDTA (ethylene diamine tetraacetic acid) was added to the electrolyte solution and the pH adjusted to between 7 and 12 (examples 7-10 in Table 1). Use of EDTA in this system requires an alkaline pH to give good mechanical properties of the oxide layer.

Calcium (Ca) Implants

The Ca implants produced by the process according to the present invention were characterised with various surface analysis techniques.

The chemical composition of the Ca implant as measured by XPS clearly reveals that calcium is a main added constituent of the surface (Ca 2p in FIG. 7). The spectrum shows a doublet peak from the Ca orbitals $2p_{1/2}$ and $2p_{3/2}$ at 351.4 eV and 347.8 eV, respectively (Ca implants) The present Ca peak positions may indicate that Ca is present in calcium titanates such as $CaTiO_3$. Also, as shown in FIG. 8, AES measurements clearly demonstrate the concentration depth distribution of Ca throughout the oxide layer, which proves that calcium/calcium compounds incorporate into the titanium oxide during said process (maybe by a mechanism of colloidal deposition). The relative atomic concentration of Ca is in the range of 0.5 to 48%.

The outer porous layer exhibits between 11% and 30% porosity, preferably about 15%. In general, porosity is defined a total area of the opening pores/a total of the scanned area×100 in %. However, in this invention, the porosity was defined as the total area of the opening pores/ the total scanned area (3×20 μm×26 μm) in %.

Figure 10:
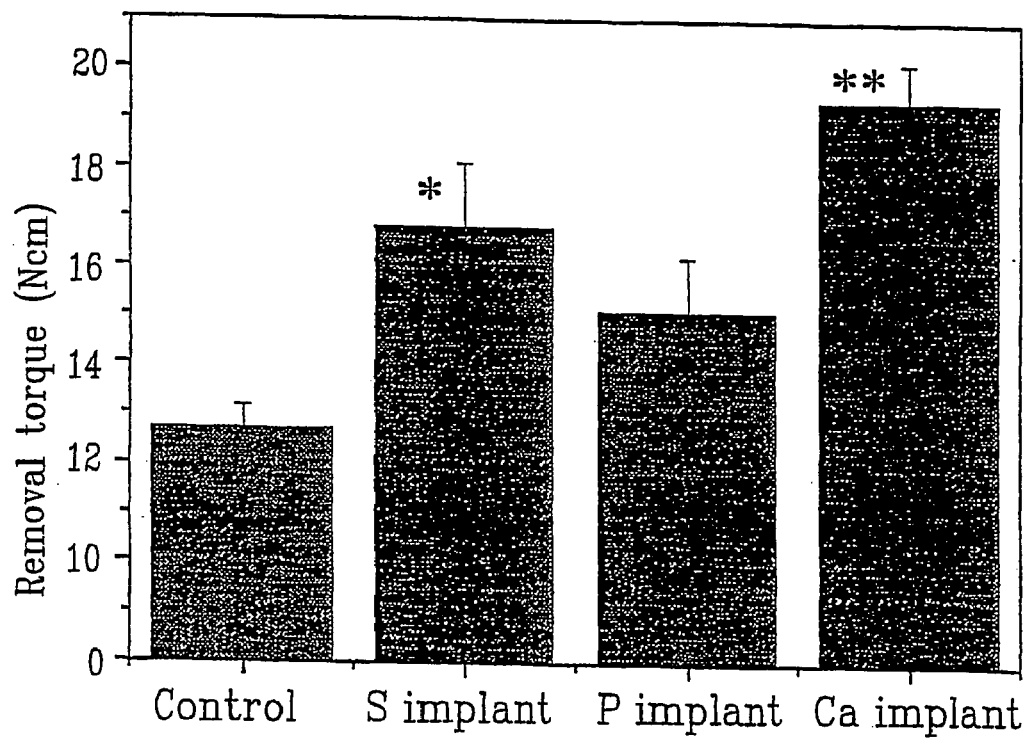
FIG. 10. shows mean values of peak removal torque measurements of the implants according to this invention compared to control implants. * indicates statistically significant differences ($p<0.05$), and ** indicates highly statistically significant differences. (Ca implants) ($p=0.0001$). Standard errors of the mean are given as bars.
Figure 11:
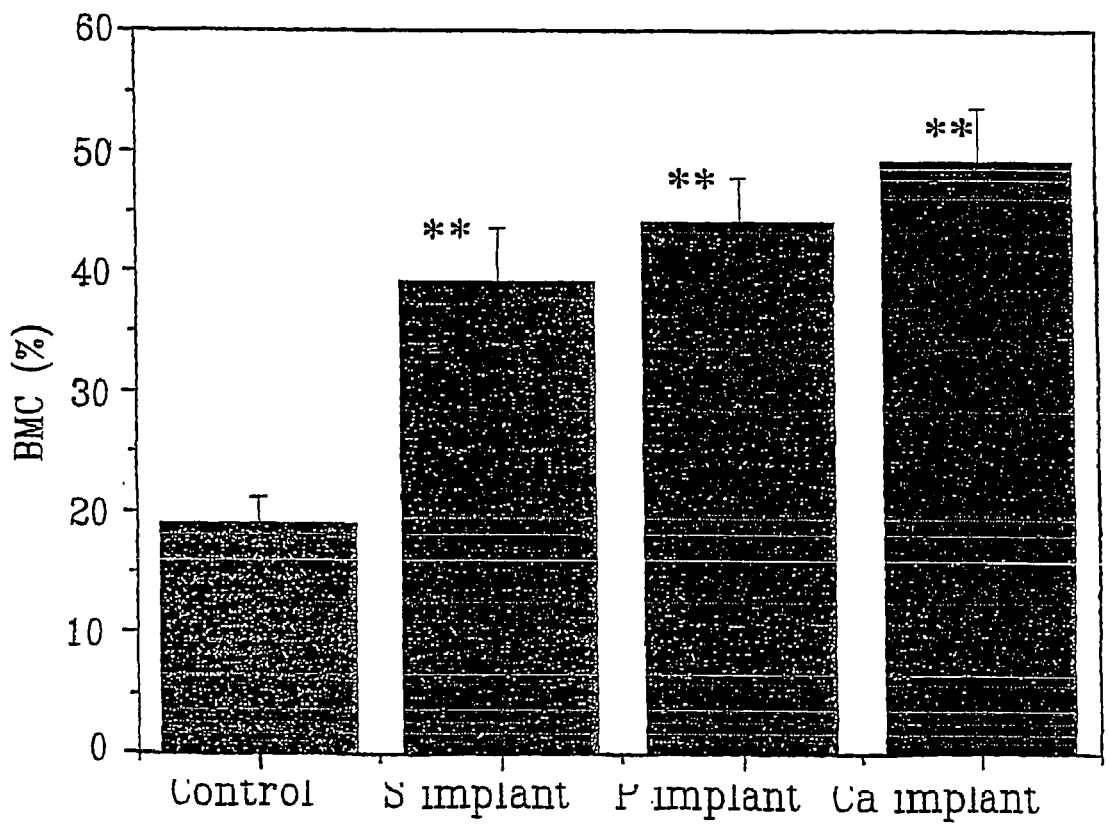
FIG. 11. shows mean values (%) of bone to metal contact (BMC) measurements of the implants according to this invention compared to control implants. ** indicates highly statistically significant differences ($p<0.001$). Standard errors of the mean (SEM) are given as bars.
Figure 12:
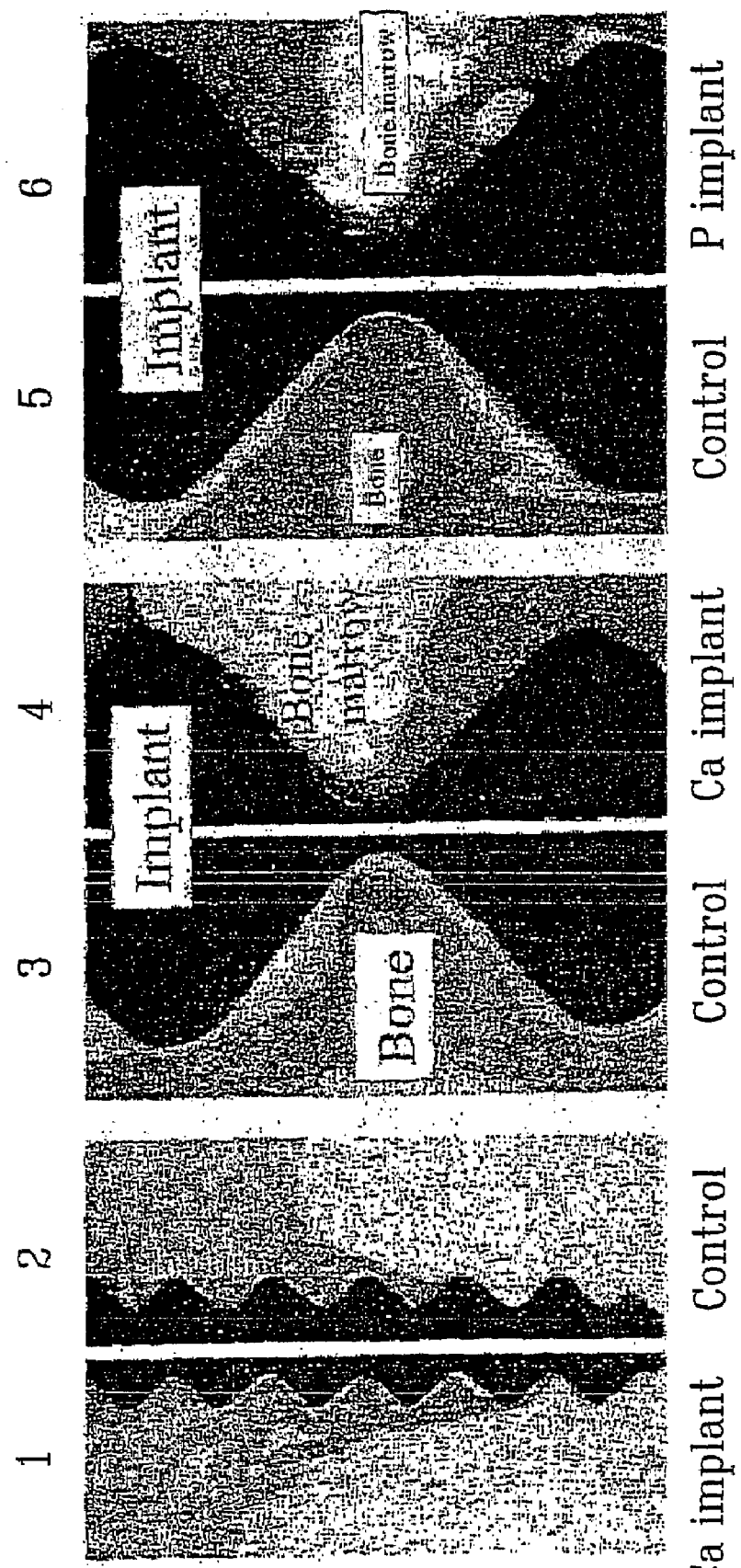
FIG. 12. shows light microscopic observations showing the much higher osteoconductive/osteoinductive properties of the present implants (1, 4, and 6) when compared to control implants (2, 3, and 5).

Osseointegration proved considerably faster and stronger for the implants according to this invention than for conventional machine-turned implants (FIGS. 10-12). Ca implants in particular demonstrated the strongest integration with bone tissue: a 240% increase of removal torque (FIG. 10). Furthermore, Ca implants also demonstrated excellent osteo-conductivity; the highest degree of mineralization and the closest direct bone to implant contact (FIG. 11), with a 273% (mean value) increase of bone to metal contact (BMC) in all implant threads (FIG. 12), and a 145% (mean value) increase in the ratio of inside to outside bone area (Inside/ Outside; %) after 6 weeks of implant insertion in rabbit model (see the experimental examples below).

Phosphorus (P) Implants

The MAO process according to the present invention can also be used for producing phosphorus-containing implants (XPS surface analyses in FIG. 7). The outer porous layer of the dual-layered oxide surface (U in FIG. 4, and FIG. 5) has a thickness below about 1000 nm, preferably 100-500 nm. The lower barrier layer (L in FIG. 4) has a thickness between about 300 nm and 2000 nm, preferably 600-1500 nm. The total thickness of both layers typically ranges from 300 to 3000 nm but should preferably be between 600 and 1500 nm (Ti and O in AES depth profile of FIG. 8). The outer porous layer exhibits between 11% and 30% porosity, preferably about 15%. The relative phosphorus concentration of the oxide layer of said implant is between 1% and 30%, preferably between 3% and 15% (P in AES depth profile of FIG. 8). The relative phosphorus concentration/amounts incorporated into the anodic oxide layer increases with layer thickness. The crystal structure is amorphous, and/or amorphous and anatase, and/or amorphous, anatase, and rutile (XRD analysis in FIG. 9).

Phosphorus-containing electrolytes used in the anodising process, singly or in any mixture, are chosen from the group consisting of: phosphoric acid, glycerophosphate, sodium phosphate, sodium pyrophosphate, sodium phosphinate, ammonium phosphate, and potassium phosphate.

Sulphur (S) Implants

Figure 9:
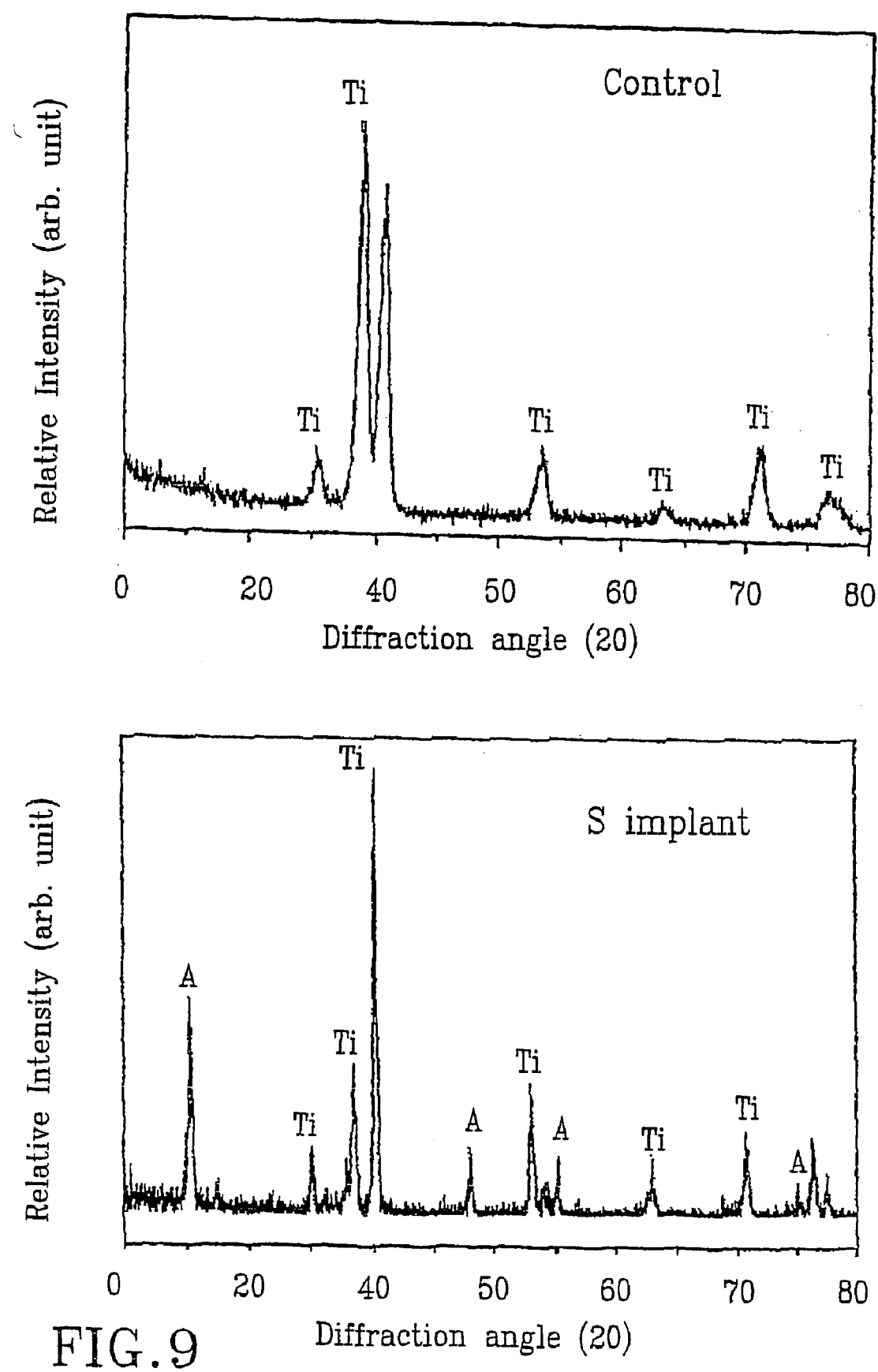
FIG. 9. shows X-ray Diffraction (XRD) angle measurements of the implants by this invention and control implants, respectively.
Figure 9:
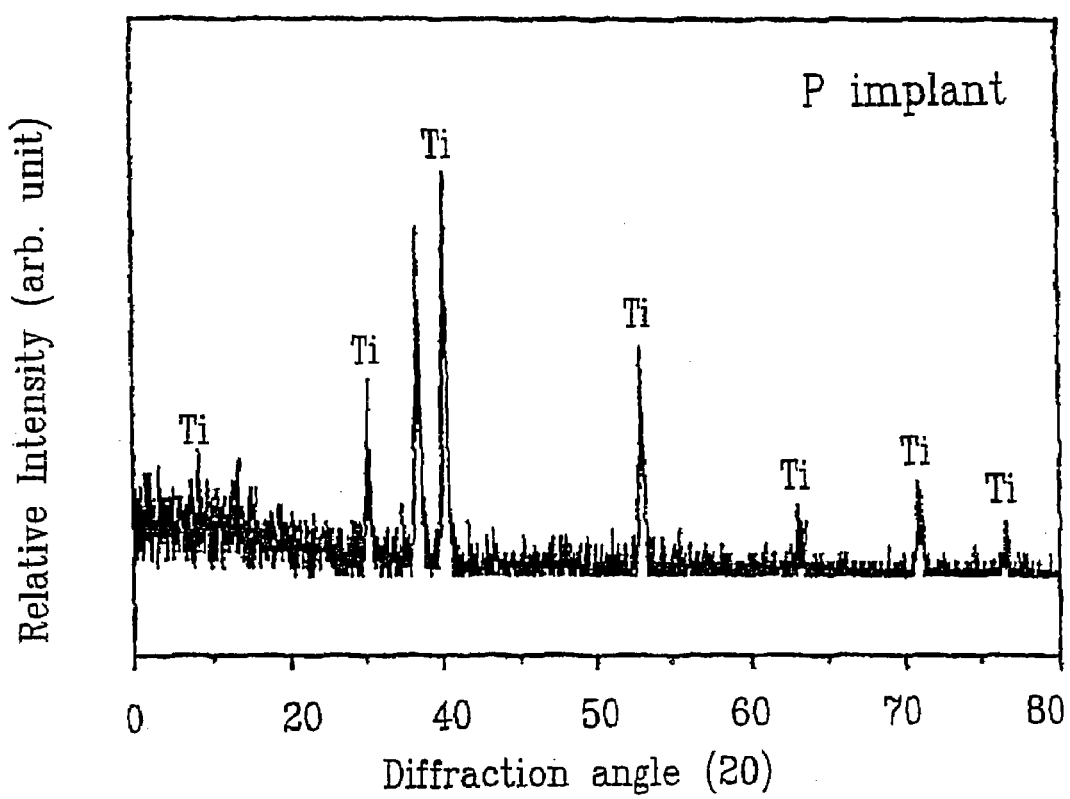
Figure 9:
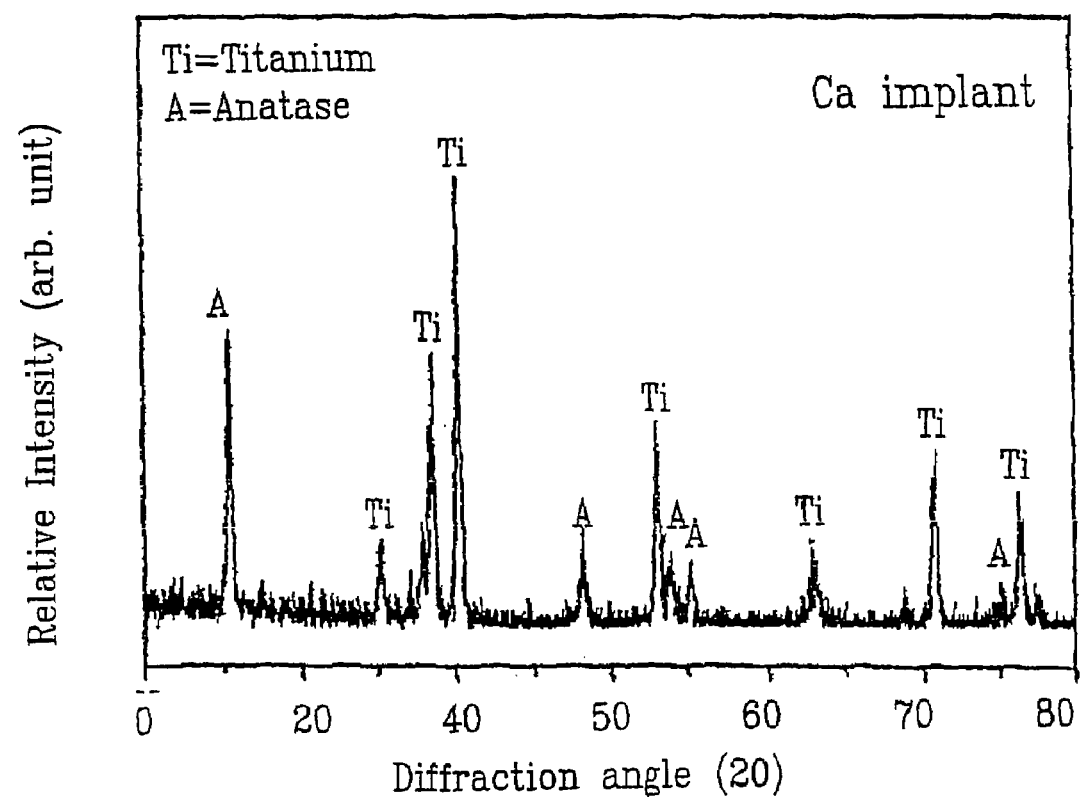

In complete analogy with the above, the MAO process according to the present invention can be used for producing implants with sulphur-containing compounds incorporated into the titanium oxide surface. The porous outer layer CU in FIG. 4, and FIG. 5) has a thickness below 1000 nm and should preferably be 100-500 nm, with a porosity between 11-30%, preferably about 15%. The lower barrier layer (L in FIG. 4) has a thickness between 300-2000 nm, preferably 600-1500 nm. Total thickness of both layers typically ranges from 300 to 3000 nm, preferably from 600 and 1500 nm (S in FIG. 8). Relative sulphur concentration of the oxide layer is between 1% and 30%, preferably between 3% and 15% (FIG. 8). The relative sulphur concentration/amounts incorporated into the anodic oxide layer increases with layer thickness. The crystal structure is amorphous, and/or amorphous and anatase, and/or amorphous, anatase, and rutile (FIG. 9).

Sulphur-containing electrolytes used in the anodising process, singly or in any mixture, are chosen from the group consisting of: sulphuric acid, potassium sulphate, sodium sulphate, sodium thiosulphate, sodium hydrosulphite, and sodium pyrosulphite.

The present invention will now be further illustrated by means of the following non-limited examples.

Experimental Section

Before the MAO process, all samples were degreased with trichlorethylene and absolute ethanol for 15 min, rinsed with absolute ethanol, and dried in an oven at 50° C. for 24 hours. The process was performed using DC power supply connected to an IBM computer in which current and voltage could be continuously recorded at intervals of 0.5 seconds (FIG. 1).

Said MAO process, from the first onset of micro arcing phenomenon on the titanium/titanium alloy anode to near anodic forming voltage transient with slope $dV/dt \approx 0.3$, absolutely depends on specified combinations of major electrochemical parameters, especially the intrinsic nature and concentration of said electrolytes, the applied current density, and the electrolyte temperature. As typical examples, the present invention controls the anodic forming voltage transient as follows: Increases of the current density and the surface area ratio of anode to cathode resulted in an increase of the anodic forming voltage transient—consequently the anodising time, required to reach anodic forming voltage transient with slope $dV/dt \approx 0.3$, becomes longer, whilst an increase of the electrolyte concentration, electrolyte temperature and agitation speed, decreases the anodic forming voltage transient—consequently, the anodising time to reach anodic forming voltage transient with slope $dV/dt \approx 0.3$, becomes shorter; decreases of the current density and the surface area ratio of anode to cathode decreases the anodic forming voltage transient—consequently, the anodising time to reach anodic forming voltage transient with slope $dV/dt \approx 0.3$, becomes shorter, whilst decreases of the electrolyte concentration, electrolyte temperature and agitation speed increase the anodic forming voltage transient—consequently, the anodising time to reach anodic forming voltage transient with slope $dV/dt \approx 0.3$, becomes longer.

Therefore, any given example of specified combinations of major electrochemical parameters, especially the intrinsic nature and concentration of said electrolytes and the applied current density, are not limitative. In any cases, however, the whole anodising time did not take more than about 120 seconds. The applied DC voltage was in the range from 30 V to 500 V The current density was in the range from 60 mA/cm$^2$ to 4000 mA/cm$^2$. The temperature was in the range from 9° C. to 100° C. The agitation speed of the electrolytes was in the range from zero rpm to 800 rpm. The surface area ratio of the screw type of titanium anode versus the platinum counter electrodes was 3.5%.

EXAMPLES 1 to 10

Electrochemical Parameters of the MAO Process

Examples 1-5 is the MAO process in single-component calcium electrolyte systems, the electrochemical parameters of which are summarized in Table 1. Said MAO process started and ended as follows: for calcium acetate, calcium lactate, and calcium sulphate the first onset of the MAO started at 10-13 s. (in the range of approximately 210-230 V), 25-30 s. (approx. 180-200 V), 8-13 s. (approx. 120-150 V), and 10-13 s. (approx. 210-230 V), respectively. The anodizing time to maintain anodic forming voltage transient with slope $dV/dt \approx 0.3$, was approximately 30-120 s., preferably 30-60 s. For electrical current densities of 60-2000 mA/cm$^2$, calcium/calcium compounds were incorporated into the anodic oxide film (maybe by a colloidal deposition mechanism). More particularly, the calcium amount of said calcium implants increased with the current density.

Figure 3:
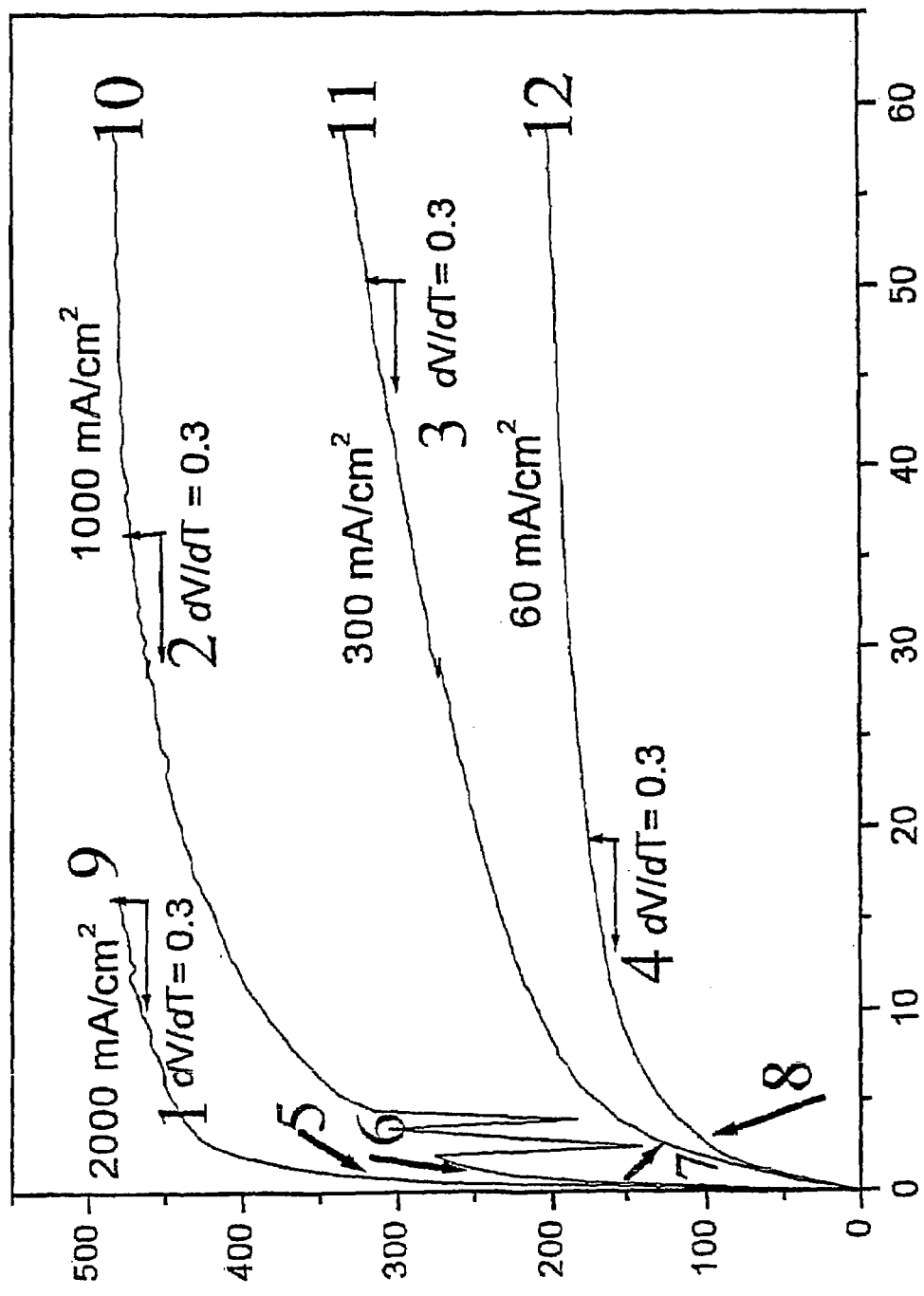
FIG. 3. shows the electrochemical oxide growth in zone 2 only, and its dependence on various parameters as described in the text (numbers 1-12). The incidenceof slope dV/dt=0.3 is indicated in each plot, as is the electric current density.

Examples 6-10 describe the MAO process performed in mixed calcium electrolyte systems, also summarized in Table 1. FIG. 3 shows the combinations of major parameters used to control the process: the chemical nature and concentration of calcium-containing electrolytes, applied current density, electrolyte temperature, and agitation speed. Setting the current density to 60 mA/cm$^2$ initiates the first onset of micro arcing phenomenon, which started at about 100 V (8 in FIG. 3) and ended up at 150 V (4 in FIG. 3). Correspondingly, for 300 mA/cm$^2$ it started at 130 V (7 in FIG. 3) and ended at 300 V (3 in FIG. 3); for 1000 mA/cm$^2$ it started at 260 V (6 in FIG. 3) and ended at 450 V (2 in FIG. 3); for 2000 mA/cm$^2$ it started at 330 V (5 in FIG. 3) and ended at 470 V (1 in FIG. 3), respectively. In all cases the process ended at $dV/dt \approx 0.3$.

TABLE 1

Calcium electrolyte systems and the electrochemical parameters applied in the present invention

| No. | Calcium-containing electrolytes | Concentration, (mol/l) | Calcium amount, (relative atom %) | Current density, (mA/cm$^2$) | Voltage (V) to reach near dV/dt = 0.3 | pH |
|---|---|---|---|---|---|---|
| 1 | calcium hydroxide | 0.1, 1.0 | 2-5 | 60, 300, 1000, 2000, 4000 | 150-500 | >7.5 |

TABLE 1-continued

Calcium electrolyte systems and the electrochemical parameters applied in the present invention

| No. | Calcium-containing electrolytes | Concentration, (mol/l) | Calcium amount, (relative atom %) | Current density, (mA/cm$^2$) | Voltage (V) to reach near dV/dt = 0.3 | pH |
|---|---|---|---|---|---|---|
| 2 | calcium acetate | 0.025, 0.15, 1.0 | 2-10 | 60, 120, 180, 2000 | 200-500 | >7.5 |
| 3 | calcium lactate | 0.1, 0.2, 0.5, 1.0 | 2-7 | 60, 120, 2000 | 180-500 | >7.5 |
| 4 | calcium sulphate | 0.1, 1.0 | 2-5 | 120, 1000 | 200-350 | >7.5 |
| 5 | calcium nitrate | 0.1, 1.0 | 0.5-0.8 | 60, 120 | 30 | >7.5 |
| 6 | calcium acetate + calcium hydroxide | 0.1 + 0.1 | 4-12 | 60, 300, 2000, 4000 | 200-500 | >7.5 |
| 7 | calcium acetate + EDTA | 0.1 + 0.15 | 5-20 | 60, 300, 1000, 2000 | 220-500 | 7.5-10 |
| 8 | calcium acetate + EDTA + malic acid | 0.1 + 0.15 + 0.1 | 8-35 | 120, 300, 1000, 2000 | 250-500 | 7.5-10 |
| 9 | calcium hydroxide + EDTA + sodium glycerophosphate | 0.1 + 0.2 + 0.001 | 10-40 | 60, 300, 1000, 2000 | 220-500 | 7.5-10 |
| 10 | calcium hydroxide + EDTA + succinic acid + sodium glycerophosphate | 0.1 + 0.2 + 0.1 + 0.001 | 15-48 | 120, 300, 2000, 4000 | 230-500 | 7.5-10 |

EXAMPLE 11

Regulation of the MAO Process

The MAO process according to the present invention is designed to regulate the intensity/extension of breakdown phenomena, using the anodic voltage transient with slope dV/dt as an important parameter. The implant preparation process is characterized by an anodic voltage surge (Table 2), visible electric sparking on the anode surface, and gas evolution.

TABLE 2

Examples of anodic voltage surge (within boxes).

| Current density = 124 mA/cm$^2$ | | Current density = 300 mA/cm$^2$ | |
|---|---|---|---|
| Time, (s) | Voltage, (V) | Time, (s) | Voltage, (V) |
| 10 | 196 | 1.5 | 260.5 |
| 10.5 | 199 | 2 | 275 |
| 11 | 200 | 2.5 | 140 |
| 11.5 | 196 | 3 | 223.5 |
| 12 | 202 | 3.5 | 305 |
| 12.5 | 204 | 4 | 183 |
| | | 4.5 | 315 |
| | | 5 | 328.5 |

EXAMPLE 12

Surface Ca, P, and S Oxide Chemistry

Surface oxide chemistry of the Ca, P, and S implants was analyzed by AES and XPS measurements [Sul et al 2001b]. High-resolution XPS spectra (FIG. 7) indicated the presence of calcium titanates such as $CaTiO_3$ at the outermost surface for Ca implants, phosphated titanium oxides (e.g. $Ti(HPO_4)_{2-x}$, $TiPO_4$, etc) for P implants, and sulphated titanium oxides (e.g. $TiSO_4$, $Ti_2(SO_4)_3$, etc) for S implants, Furthermore, depth profiles by AES measurements in FIG. 8 obviously showed that Ca, P and S are incorporated throughout the titanium oxide layer by said MAO process.

EXAMPLE 13

Transmission Electron Microscopy (TEM) Cross-sectional View

The oxide films were crosscut using an ultramicrotome and the morphological structure, as seen in the TEM cross-sectional view of FIG. 4, demonstrated a double structure. The upper porous layer (U in FIG. 4) was characterised by a lot of craters and is much thinner than the lower layer (L in FIG. 4). Furthermore, the lower barrier layer did not include any pores/craters, extension of pore channels, network of channels or connected channel branches.

EXAMPLE 14

Oxide Thickness

The oxide thickness was measured with TEM and AES. The thickness of the calcium containing oxide layer consisted of the upper porous layer (U in FIG. 4)+the lower barrier layer (L in FIG. 4). Total thickness of one calcium containing oxide layer, measured by the TEM cross-sectional view of FIG. 4, was approximately 300 nm; about 100 nm of U and 200 nm of L. In another example shown in FIG. 8, the oxide thickness of Ca, P, and S implants is 1296±225 nm, 1224±144 nm, and 1080±324 nm, respectively, measured with AES at one thread-top, one thread-valley, and in the bottom of the screw implant.

EXAMPLE 15

Crystal Structure

A thin-film X-ray diffractometer (TF-XRD, Rigaku Co.), equipped with a PW3020 goniometer was employed for analyses of the titanium oxide crystal structure. Angles were scanned between 20° and 80° with a step size of 0.04°. Spectra were recorded using Cu Kα radiation (wavelength 1.54 Å). Crystal structures of said calcium implants showed amorphous, anatase, and a mixture of anatase and rutile structures (FIG. 9).

EXAMPLE 16

Surface Roughness

The surface roughness was measured with confocal laser scanning profilometer TopScan3D®) as described by Wennerberg et al. The surface roughness parameter $S_a$ (the height deviation from the mean plane) was 0.83±0.32 µm for control implants, 1.04±0.42 µm for S implants, 0.82±0.29 µm for P implants, and 0.85±0.32 µm for Ca implants. The corresponding $S_{cx}$ values (the average distance between surface irregularities in the spatial direction) were 9.78±1.40 µm, 12.05±3.74 µm, 11.19±2.33 µm, 9.83±1.07 µm, respectively.

Animal Studies

Said Ca, P, and S implants, produced by said process, demonstrated much faster and stronger osseointegration as compared to conventional machine-turned implants. Ten mature (average age was 10 months) New Zealand white rabbits of both sexes were used. Each rabbit had three implants inserted in each tibia and one implant in each femur. After 6 weeks of healing time, evaluation of the bone tissue reactions to implants was performed in terms of a biomechanical test and histomorphometry. Both have been most widely accepted as excellent techniques to prove the bone to implant integration (osseointegration) in in vivo animal studies since the 1980's. Statistical analyses of the removal torque measurements were performed using the Tukey test for the purpose of multiple comparisons. The histomorphometric quantifications were analysed using Wilcoxon Signed Rank Test.

EXAMPLE 17

Biomechanical Test (Removal Torque)

In removal torque techniques the applied counter-torque needed to unscrew the implant is measured. The electronic equipment used allowed torque analysis of the peak loosening torque [Johansson et al. 1998]. The Ca implants demonstrated the strongest bone response regarding removal torque test. S and P implants also showed significantly stronger bone tissue reactions in comparison to controls. As shown in FIG. 10, the multiple comparisons of the mean values between all implant groups demonstrated significant difference between test S implants vs controls (p=0.022) and highly significant differences between test Ca implants vs controls (p=0.0001). The mean peak values of the removal torque measurements were 16.8 Ncm (±4.5; range 10-25 Ncm) for S implants (n=12), 15.1 Ncm (±4.3; range 9-20 Ncm) for P implants (n=16), 19.4 Ncm (±3.1; range 14-24 Ncm) for Ca implants, and 12.7 Ncm (±1.9; range 10-15 Ncm) for control implants (n=15).

EXAMPLE 18

Histomorphometry

The histomorphometrical investigations involved (i) quantifications of the bone to metal contact (BMC) and (ii) the evaluation of tissue remodelling activity (a rough estimate of the osteoconductivity) [Johansson et al. 1998 and Sul et al 2001b]. Routinely stained undecalcified Toluidine blue sections (10-30 µm thick) were histomorphometrically analysed with a Leitz Aristoplan light microscope, which was equipped with a Leitz Microvid unit, connected to a PC, enabling the observer to perform quantifications directly in the eye-piece of the microscope, using a magnification of 10× and a zoom of 2.5×. The Ca implant demonstrated the strongest bone response regarding quantitative histomorphometry. The increase of mean BMC values revealed 272% in Ca implants, 232% in P implants, and 186% in S implants when compared to the paired control groups. Said Ca, P, and S implants (FIG. 11) showed much higher osteoinductive properties than machine-turned oxide surface of non-treated implants. Histological findings (FIG. 12) clearly showed that on the modified surfaces, and most particularly the Ca implant surfaces, the bone in close contact to the implant surface was more homogeneous and much more densely mineralised while the control surface demonstrated a lot of osteoid layers and was less mineralised as seen by the staining reactions. Apposition of new bone along said implant surfaces was more diffusely spread in comparison with control implants. This indicates the superior osteoconductivity of said implants, especially Ca implants.

EXAMPLE 19

Reinforcement of Mechanical Properties

The mechanical strength of the oxide layer of anodised implants is an essential requirement for the usefulness and safety of clinical applications. Calcium-containing oxides made by said MAO process demonstrated excellent mechanical strength. The tensile strength of said oxide layer was shown to be 62 MPa (Table 3), which almost corresponds to a 100% increase compared to 33 MPa of SE 9901974-7 and to the range of 30 to 35 MPa of U.S. Pat. No. 5,478,237 A.

TABLE 3

Test of tensile strength for the Ca Implant

| Sample | Surface area of titanium disc (cm$^2$) | Strain, (MPa) |
|---|---|---|
| 1 | 4.9 | 57 |
| 2 | 4.9 | 62 |
| 3 | 4.9 | 65 |
| 4 | 4.9 | 63 |
| Mean | | 62 |
| Standard deviation | | 3 |

Oxidised implants having thicker oxide layers than the present calcium implants (more than 5 µm, as formed below dV/dt<0.3 in zone 3 of FIG. 2), showed a delamination of the oxide film and oxide wear particles scattered near the implant surface (maybe due to tear-off of the thicker oxide films) internalised by the inflammatory cells such as macrophages and multinuclear giant cells (FIG. 6a). As a matter of fact, the thicker oxide layer obtained in or above zone 3 showed inferior mechanical properties such as microcracks (e in FIG. 2). Other oxidised implants having thinner oxide layers with thickness of 202±53 nm, 608±127 nm, and 805±112 nm formed in zones 1 and 2 (a and b in FIG. 2) did not show "tear off" of the oxide film and no oxide wear particles could be detected.

Figure 6B:
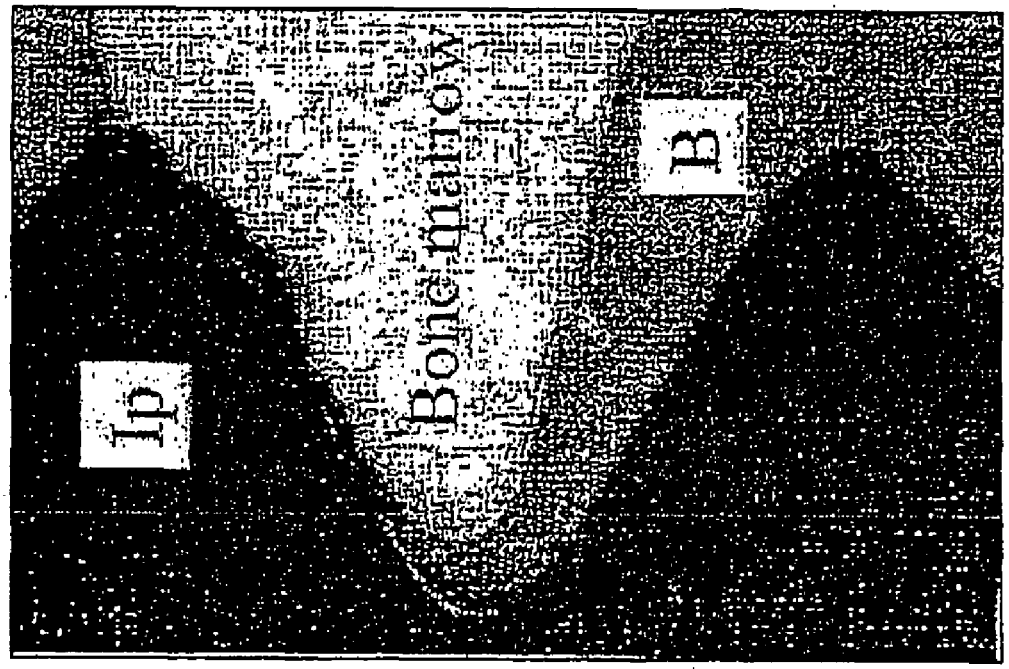
FIG. 6. shows Light microscopic comparison between an implant produced by conventional anodic oxidation (FIG. 6a) and a calcium-containing implant according to the present invention (FIG. 6b). In 6a internalised oxide particles (arrows) are clearly visible in macrophages but no oxide particles are present in 6b. The implants by this invention also exhibit superior osteoconductivity (larger area of bone to implant contact). Bar=100 μm. Ip=implant, B=bone FIG. 7. shows High resolution X-ray Photoelectron Spectroscopy (XPS) at the Ca $2p_{1/2}$, P $2p_{3/2}$, and S 2p peak positions of the Ca, P, and S implants, respectively.
Figure 6A:
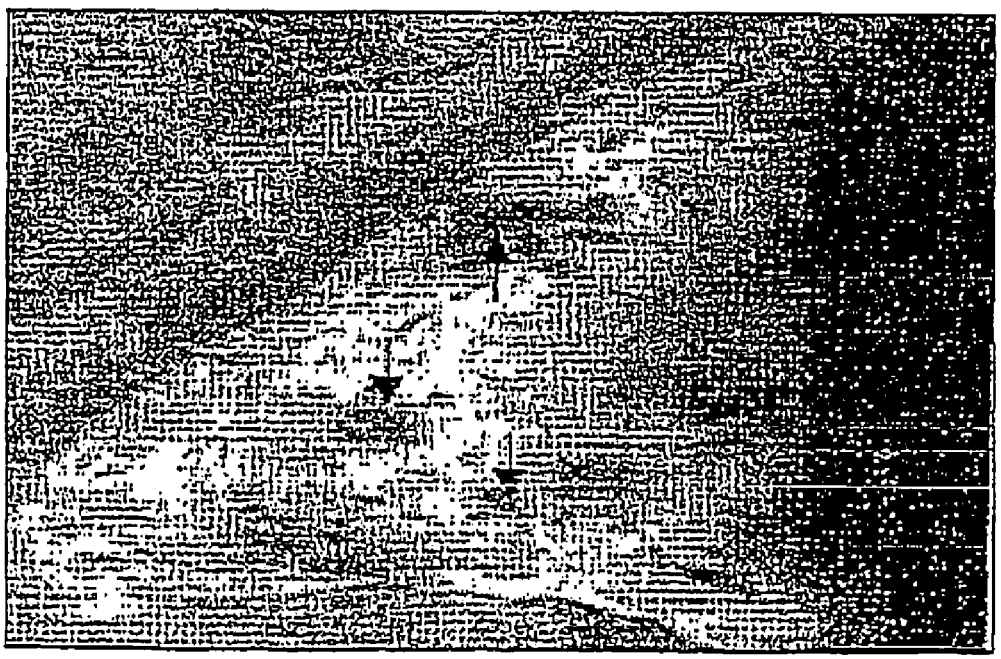

However, the calcium-containing oxides made by said MAO process demonstrated superior mechanical strength and osseointegration properties, better than any implant tested so far, and did not exhibit a delamination or oxide particles formation (FIG. 6b).

EXAMPLE 20

Measurement of the Porosity

The porosity was defined as the total area of the opening pores/the total scanned area (3×20 μm×26 μm) in %. In the table below the pore characteristics of screw implants is shown.

The data was obtained using an image analysis of Scanning Electron Microscopy (SEM) negatives on 3 randomly selected areas with a scanning area of 20 μm×26 μm.

TABLE 4

| Sample | PSD[1] | Porosity (%)[2] | Pore number[3] |
|---|---|---|---|
| Group I | 1.27 μm², ≦8 μm | 12.7 | 156 |
| Group II | 1.53 μm², ≦8 μm | 24.4 | 245 |
| Group III | 2.10 μm², ≦8 μm | 18.7 | 139 |

[1]Pore size distribution (PSD) was presented by opening area and by diameter.
[2]Porosity defined as the total area of the opening pores/the total scanned area 3 × 20 μm × 26 μm in %
[3]Pore number counted in the scanning area of 3 × 20 μm × 26 μm.

The invention shall not be regarded as being limited to the above embodiments and examples, but shall be interpreted within the scope of the appended claims.

REFERENCES

Adell R. et al. *Int J Oral Maxillofac Impl* 5, 347-359 (1990)
Kasemo B. and Lausmaa J. *Swedish dental journal*, Suppl. 28, 19-36 (1983).
Johansson C. B. et al. *Int. J. Oral. Maxillofac. Implants* 13, 315-321(1998)
Li J. et al. In: Black J, Hastings G, (eds). *Handbook of Biomaterial Properties*. London: Chapman & Hall; 340-354 (1998)
Hench L. et al. *Chem Rev* 90:33-72 (1990)
Albrektsson T. J. *Oral Maxillofac Surg* 56:1312-1326 (1998)
Gottlander M. et al. *Clin Oral Implant Res* 8: 345-351 (1997)
Sul Y. T. et al. *Med. Eng. Phys*, 23, 329-346 (2001a)
Sul Y. T. et al. *J Mater Sci-Mater Med;* 12:1025-1031 (2001b)
Hala J. and Lausmma *J. Applied Osseointegration Research* 1: 5-8 (2000)
Michiaki H et al. *Altobia*, 1, (1989)
Seishiro I. *Color material*, 62, (1989)
Wennerberg A et al., *J Biomed Eng;* 14:412-418 (1992)

The invention claimed is:

1. Osteoconductive/osteoinductive titanium/titanium alloy implant comprising:
  a titanium oxide with anodic incorporation of an additional element,
  said additional element being a single one element chosen from the group consisting of calcium, phosphor and sulphur, wherein,
  said implant exhibits a cross-section of an osteoconductive/osteoinductive oxide layer, which consists of a double layer structure of an upper porous layer of the titanium oxide with anodic incorporation of the additional element and a lower compact barrier layer of the titanium oxide with anodic incorporation of the additional element,
  wherein the lower barrier layer comprises less of said additional element than the upper porous layer, and the upper porous layer exhibits more than about 11% porosity and less than about 30%.

2. Implant according to claim 1, wherein the porous upper layer exhibits an open structure comprising a plurality of shallow craters.

3. Implant according to claim 1, wherein the upper layer has a thickness below about 1000 nm.

4. Implant according to claim 1, wherein the lower barrier layer has a thickness ranging between about 300 nm and 2000 nm.

5. Implant according to claim 1, wherein the thickness of said osteoconductive/osteoinductive double layer-structured oxide containing an additional element is from 300 to 3000 nm.

6. Implant according to claim 1, wherein the lower barrier layer does not include any pores/craters or channels.

7. Implant according to claim 1, wherein the upper layer has a thickness in the range of 100-500 nm.

8. Implant according to claim 1, wherein the lower barrier layer has a thickness ranging between in the range of 600-1500 nm.

9. Implant according to claim 1, wherein the thickness of said osteoconductive/osteoinductive double layer-structured oxide containing an additional element is between 800 and 1500 nm.

10. Osteoconductive/osteoinductive titanium/titanium alloy implant comprising:
  a titanium oxide with anodic incorporation of an additional element,
  said additional element being a single one element chosen from the group consisting of calcium, phosphor and sulphur, wherein,
  said implant exhibits a cross-section of an osteoconductive/osteoinductive oxide layer, which consists of a double layer structure of an upper porous layer of the titanium oxide with anodic incorporation of the additional element and a lower compact barrier layer of the titanium oxide with anodic incorporation of the additional element,
  wherein the lower barrier layer comprises less of said additional element than the upper porous layer,
  wherein the crystal structure of titanium oxide is amorphous and/or amorphous and anatase and/or amorphous, anatase and rutile.

11. Osteoconductive/osteoinductive titanium/titanium alloy implant comprising:
  a titanium oxide with anodic incorporation of an additional element,
  said additional element being a single one element chosen from the group consisting of calcium, phosphor and sulphur, wherein,
  said implant exhibits a cross-section of an osteoconductive/osteoinductive oxide layer, which consists of a double layer structure of an upper porous layer of the titanium oxide with anodic incorporation of the additional element and a lower compact barrier layer of the titanium oxide with anodic incorporation of the additional element,
  wherein the lower barrier layer comprises less of said additional element than the upper porous layer,
  wherein the relative concentration of the additional element incorporated into the anodic oxide layer formed on titanium/titanium alloy implants increases with the thickness of the oxide layer containing an additional element.

12. Osteoconductive/osteoinductive titanium/titanium alloy implant comprising:
- a titanium oxide with anodic incorporation of an additional element,
- said additional element being a single one element chosen from the group consisting of calcium, phosphor and sulphur, wherein,
- said implant exhibits a cross-section of an osteoconductive/osteoinductive oxide layer, which consists of a double layer structure of an upper porous layer of the titanium oxide with anodic incorporation of the additional element and a lower compact barrier layer of the titanium oxide with anodic incorporation of the additional element,
- wherein the lower barrier layer comprises less of said additional element than the upper porous layer,
- wherein the relative concentration of the additional element in of the oxide layer of said implant is between 1% and 50%.

13. Osteoconductive/osteoinductive titanium/titanium alloy implant comprising:
- a titanium oxide with anodic incorporation of an additional element,
- said additional element being a single one element chosen from the group consisting of calcium, phosphor and sulphur, wherein,
- said implant exhibits a cross-section of an osteoconductive/osteoinductive oxide layer, which consists of a double layer structure of an upper porous layer of the titanium oxide with anodic incorporation of the additional element and a lower compact barrier layer of the titanium oxide with anodic incorporation of the additional element,
- wherein the lower barrier layer comprises less of said additional element than the upper porous layer,
- wherein the upper porous layer exhibits more than about 11% porosity and less than about 15%.

14. Osteoconductive/osteoinductive titanium/titanium alloy implant comprising:
- a titanium oxide with anodic incorporation of an additional element,
- said additional element being a single one element chosen from the group consisting of calcium, phosphor and sulphur, wherein,
- said implant exhibits a cross-section of an osteoconductive/osteoinductive oxide layer, which consists of a double layer structure of an upper porous layer of the titanium oxide with anodic incorporation of the additional element and a lower compact barrier layer of the titanium oxide with anodic incorporation of the additional element,
- wherein the lower barrier layer comprises less of said additional element than the upper porous layer,
- wherein the relative concentration of the additional element in of the oxide layer of said implant is between 1% and 25%.

* * * * *